United States Patent [19]

Collins et al.

[11] Patent Number: 4,747,310

[45] Date of Patent: May 31, 1988

[54] PROBE FOR COMPOSITE ANALYZER TESTER

[75] Inventors: Richard M. Collins, East Setauket; Richard F. Chance, Bayport, both of N.Y.

[73] Assignee: Grumman Aerospace Corporation, Bethpage, N.Y.

[21] Appl. No.: 895,790

[22] Filed: Aug. 12, 1986

[51] Int. Cl.$^4$ .......................................... G01N 29/04
[52] U.S. Cl. ........................................ 73/661; 73/643
[58] Field of Search .............. 73/661, 643, 629, 597, 73/570, DIG. 1

[56] References Cited

U.S. PATENT DOCUMENTS 3,403,547 10/1968 Schwartz .............................. 73/661
4,307,611 12/1981 Opara ................................... 73/629
4,523,473 6/1985 Chamuel ............................... 73/643

Primary Examiner—Anthony V. Ciarlante
Attorney, Agent, or Firm—Scully, Scott, Murphy & Presser

[57] ABSTRACT

A composite analyzer probe, for use with a composite analyzer tester instrument for nondestructively testing and analyzing the physical properties and gaging the thickness of a test material. A cylindrical probe housing has a generally flat end surface designed to be placed flat against the surface of the test material. An annular magnetic induction coil is positioned against the end surface, a piezoelectric element having a hollow cylindrical casing is positioned within the annular magnetic induction coil, and an eddy current coil is positioned within the piezoelectric cylindrical casing. The single improved probe allows four different measurements to be taken at one location on the test material without any required movement or replacement of the probe.

3 Claims, 2 Drawing Sheets

PROBE FOR COMPOSITE ANALYZER TESTER

BACKGROUND OF THE INVENTION

1. Field of the Invention

The present invention relates generally to an improved probe for a composite analyzer tester for nondestructively testing and analyzing materials, and more particularly pertains to an improved probe for a composite analyzer tester for nondestructively analyzing the physical properties and gaging the thickness of advanced graphite-resin composite materials. Such graphite-resin composite materials are being utilized with a greater frequency of application in the construction of airplane components, such as for the aircraft skin and in other substructural components thereof.

2. Discussion of the Prior Art

The nondestructive testing of advanced fiber-matrix materials, such as graphite-resin composite materials and components, has been developed to provide a high level of assurance of the quality and structural integrity of such materials and components. The individual fiber and matrix material components that make up such a composite are often of non-uniform quality and moreover are laminated in different and varied patterns. Additionally, fabricators can be expected to make occasional human errors in the number and spacing of plies in the layup. Slight changes in curing cycles and rates of heating can also have major effects on mechanical properties, but no obvious effect on the visual appearance of the finished parts. In general, the deviation in properties for composite materials on multiple tests is far greater than considered acceptable for established metal technology. Refined and improved nondestructive testing apparatus and methods must be developed to allow inspection to establish, with greater assurance, the exact quality of the part under surveillance.

Many individual inspection, testing and analysis techniques have been developed for such fiber-matrix materials, such as by acoustic emission, radiographic testing, ultrasonic testing, magnetic induction testing, electrical conductivity testing, testing by liquid penetrants, thermal infrared testing, and by visual inspections thereof.

Related patent application for a Composite Analyzer Tester U.S. Ser. No. 895,789, filed Aug. 12, 1986, commonly assigned herewith, discloses a composite analyzer tester instrument having three separate probes, a magnetic induction probe, an ultrasonic pulse-echo probe, and an eddy current probe, which are used in succession to take four separate measurements of different properties of a test material. An instrument of this type requires the expense of three separate different probes, and requires the user to accurately place all three probes at the same location on the test material in successive measurements.

SUMMARY OF THE INVENTION

Accordingly, it is a primary object of the present invention to provide an improved probe for a composite analyzer tester instrument capable of nondestructively analyzing and testing several different properties of fiber-matrix materials, such as graphite-resin materials, such as the thickness, sonic velocity, relative sonic amplitude and relative conductivity thereof.

In accordance with the teachings herein, the present invention provides an improved probe for a composite analyzer tester for nondestructively testing and analyzing the physical properties and gaging the thickness of a test material. The improved probe includes a probe housing having a generally flat end surface designed to be placed flat against the surface of the test material. A magnetic induction coil is positioned against the end surface with the central longitudinal axis of the coil extending substantially perpendicular thereto. A piezoelectric element is positioned adjacent to the magnetic induction coil and against the end surface also, and an eddy current coil is positioned adjacent to both the magnetic induction coil and the piezoelectric element and against the end surface also, with the central longitudinal axis of the eddy current coil extending substantially perpendicular thereto.

In greater detail, the magnetic induction coil comprises an annular coil, the piezoelectric element has an annular casing positioned within the annular magnetic induction coil, and the eddy current coil is positioned within the annular casing, such that all of those elements are positioned concentrically with respect to each other at the flat end of the probe housing. Moreover the probe housing comprises a cylindrically shaped housing having the annular magnetic induction coil, the piezoelectric element, and the eddy current coil all mounted therein at a flat end thereof.

BRIEF DESCRIPTION OF THE DRAWINGS

The foregoing objects and advantages of the present invention for an improved probe for a composite analyzer tester may be more readily understood by one skilled in the art with reference being had to the following detailed description of a preferred embodiment thereof, taken in conjunction with the accompanying drawings wherein like elements are designated by identical reference numerals throughout the several views, and in which.

DETAILED DESCRIPTION OF THE DRAWINGS

Figure 1:
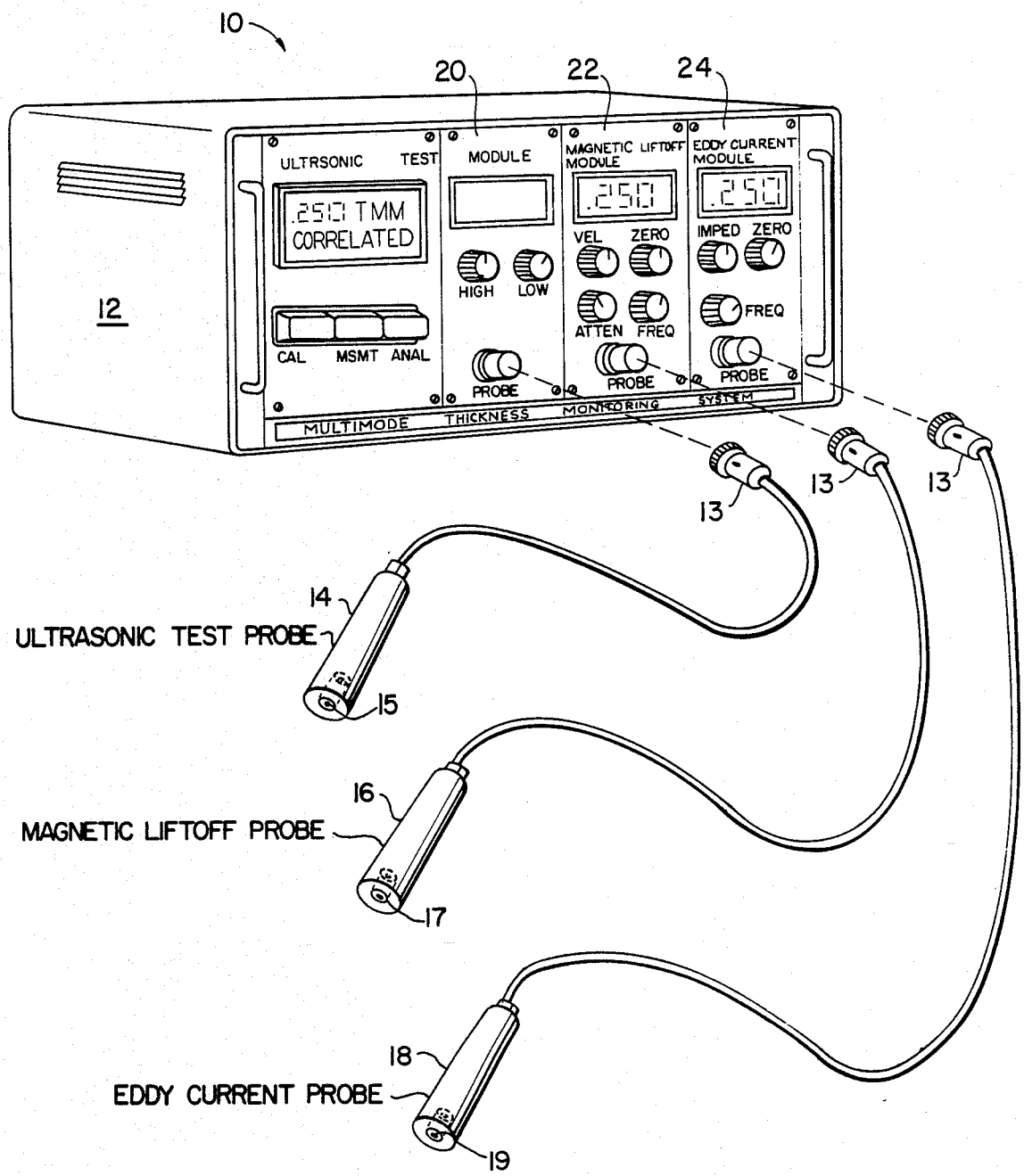
FIG. 1 is a front perspective view of a known embodiment of a composite analyzer tester instrument, and illustrates also the three different probes utilized therewith in the several tests and measurements performed by the instrument.

Referring to the drawings in detial, FIG. 1 illustrates a known embodiment of a Composite Analyzer Tester (CAT) instrument 10 for nondestructively analyzing the physical properties and gaging the thickness of advanced graphite-resin composites. The CAT instrument 10 is capable of performing four various modes of ultrasonic, magnetic, and electrical (eddy current) tests, on a graphite-resin composite, and is integrated into one convenient, portable cabinet 12. All testing is conducted by consecutively placing probes 14, 16, and 18, all of which are connected to the instrument 10 by plug jacks 13, on a particular surface location of the material.

The CAT instrument 10 consists of four systems of analysis/gaging circuitry:

System 1: RELATIVE AMPLITUDE—A microprocessor-based ultrasonic pulse-echo circuit module 20 measures the change in the amplitude of an ultrasonic pulse making a round trip (reflected as an echo) through the material. This measurement is made with the probe 14.

System 2: VELOCITY—The microprocessor-based ultrasonic pulse-echo circuit module 20 simultaneously measures the ultrasonic velocity of the material (and also uses the probe 14) while System 1 is measuring the echo relative amplitude.

System 3: THICKNESS—A low frequency, microprocessor-based, magnetoinduction circuit module 22 measures the mechanical thickness of the graphite composite, without reacting to the properties or variation in the properties of the composite. A ferromagnetic sheet of uniform magnetic permeability is placed in firm and intimate contact with the opposite surface of the composite in order to make this measurement. This measurement is made with the probe 16.

System 4: CONDUCTIVITY—A high frequency, microprocessor-based eddy current circuit module 24 is designed to measure the relative electrical conductivity or relative electrical conductance of the graphite composite. The test frequency and an eddy current probe 18 are designed to minimize "thickness effects" at the thinner end of the expected thickness range for the composites.

The magnetic induction probe 16 includes a magnetic induction coil 17 which is placed adjacent to the outer surface of the test material such that the central longitudinal axis of the coil is generally perpendicular to the surface of the material. While using this circuit, an element of uniform magnetic permeability is placed in close contact with the inner surface of the test material, opposite the placement of the magnetic induction probe 16 on the outer surface thereof, to complete a magnetic circuit with the magnetic induction coil 17, with the test material being located therebetween. The magnetic induction circuit then energizes the magnetic induction coil at a relatively low frequency of approximately fifty kilohertz. In this arrangement, the test material essentially acts as a spacer between the coil and the element, and the distance therebetween determines the impedance of the magnetic circuit, such that a measurement thereof is also representative of the thickness of the test material.

The measured thickness is then utilized by the pulse-echo circuit in its measurement of the ultrasonic velocity in the material, and can be entered therein automatically through the microprocessor or manually. The acoustic probe 14 preferably comprises a piezoelectric transducer 15 which is initially pulsed to produce an ultrasonic pulse, and which is then monitored for detection of the echoed ultrasonic pulse. The ultrasonic pulse circuit preferably energizes the piezoelectric transducer with pulses at a frequency of approximately five megahertz. The pulse-echo circuit takes two separate measurements, the acoustic or sonic velocity through the test material, and also the attenuation of each pulse traversing the test material to its opposite surface and being reflected therefrom as an echo back to the probe.

The last measurement is by the eddy current circuit, and for this measurement the eddy current probe 18 is placed at the same location as the previous two probes. The eddy current probe 18 includes an eddy current coil 19 which is placed adjacent to the outer surface of the test material such that the central longitudinal axis of the coil is generally perpendicular to the surface of the material. The coil is then energized at a relatively high frequency above one megahertz to generate an alternating magnetic field which induces an alternating electric field in the test material having eddy currents and an alternating magnetic field associated therewith, with the associated magnetic field affecting the alternating magnetic field of the eddy current coil, such that the resultant impedance of the eddy current coil in the eddy current circuit provides a measurement of the electrical conductivity of the test material.

Figure 2:
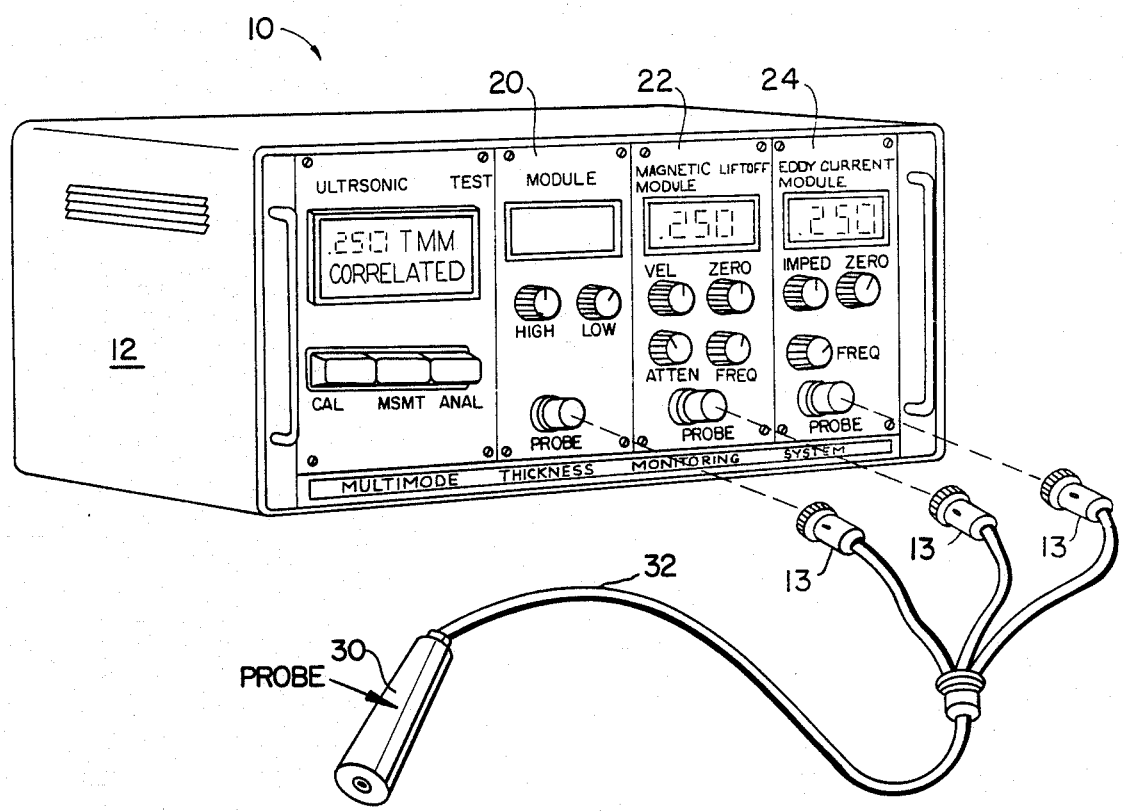
FIG. 2 illustrates the known composite analyzer tester of FIG. 1 utilizing an improved probe constructed pursuant to the teachings of the present invention.

FIG. 2 illustrates the known composite analyzer tester 10 of FIG. 1 utilizing an improved probe 30 constructed pursuant to the teachings of the present invention. The improved probe 30 is connected to the unit 10 by plug jacks 13, similar to the arrangement of FIG. 1, but the individual electrical connectors are then joined in one cable 32 leading to the improved probe 30.

Figure 3:
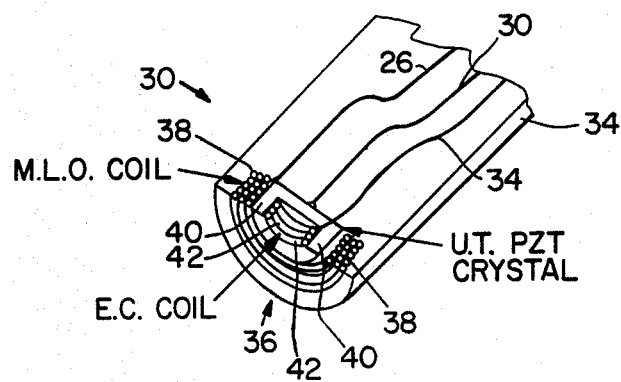
FIG. 3 is a partially sectioned view of only the improved probe of FIG. 2, illustrating details of the construction thereof.

FIG. 3 is a partially sectioned view of the improved probe 30, illustrating details of the construction thereof. The improved probe comprises a clyindrical probe housing 34 having a generally flat end surface 36 designed to be placed flat against the surface of the test material. A ralatively large annular magnetic induction coil 38 is positioned against the end surface with the central longitudinal axis of the coil extending substantially perpendicular thereto. A piezoelectric element 40 having an annular casing is positioned concentrically within the magnetic induction coil 38 and also against the end surface 36. An annular eddy current coil 42 is positioned concentrically within the piezoelectric element 40, also against the end surface 36, with the central longitudinal axis of the eddy current coil extending substantially perpendicular thereto. In this arrangement, the magnetic induction coil 38, the annular casing 40 of the piezoelectric element, and the eddy current coil 42 are all positioned concentrically with respect to each other at the flat end 36 of said probe housing.

The operation of the improved probe 30 is similar to that of the arrangement of FIG. 1, in that the magnetic induction coil 38, the piezoelectric element 40, and the eddy current coil 42 are sequentially energized. However, only one probe is utilized, thus eliminating any problems with proper positioning of multiple probes.

While a preferred embodiment of the present invention for an improved probe for a composite analyzer tester is described in detail herein, it should be apparent that the disclosure and teachings of the present invention will suggest many alternative designs to those skilled in the art. For instance, the relative concentric positions of the coils 38 and 42 and the cylindrical element 40 can be different in alternative embodiments.

What is claimed is:

1. A composite analyzer probe, for use with a composite analyzer tester for nondestructively testing and analyzing the physical properties and gaging the thickness of a test material, comprising a probe housing having a generally flat end surface designed to be placed flat against the surface of the test material, a magnetic induction coil positioned against said end surface with the central longitudinal axis of the coil extending substantially perpendicular thereto, a piezoelectric element positioned adjacent to said magnetic induction coil and against said end surface, and an eddy current coil positioned adjacent to both said magnetic induction coil and said piezoelctric element and against said end surface, with the central longitudinal axis of the eddy current coil extending substantially perpendicular thereto.

2. A composite analyzer probe as claimed in claim 1, said magnetic induction coil comprising an annular coil, said piezoelectric element comprising an annular casing positioned within said annular magnetic induction coil, and said eddy current coil being positioned within said annular casing, such that said magnetic induction coil, said annular casing of the piezoelectric element, and said eddy current coil are all positioned concentrically with respect to each other at the flat end of said probe housing.

3. A composite analyzer probe as claimed in claim 2, said probe housing comprising a cylindrically shaped housing having said annular magnetic induction coil, said piezoelectric element, and said eddy current coil all mounted therein at said flat end thereof.

* * * * *